United States Patent
Babaev

(10) Patent No.: US 6,964,647 B1
(45) Date of Patent: Nov. 15, 2005

(54) NOZZLE FOR ULTRASOUND WOUND TREATMENT

(76) Inventor: Ellaz Babaev, 5564 Bimini Dr., Minnetonka, MN (US) 55343

(*) Notice: Subject to any disclaimer, the term of this patent is extended or adjusted under 35 U.S.C. 154(b) by 257 days.

(21) Appl. No.: 09/684,044

(22) Filed: Oct. 6, 2000

(51) Int. Cl.⁷ ............................................. A61B 17/20
(52) U.S. Cl. ........................................ 604/22; 601/2
(58) Field of Search ............................. 604/22, 20, 24, 604/890.1, 509, 49, 66, 68–73, 289, 290; 128/200.14, 200.16; 606/3, 9, 10, 13; 607/50, 607/81, 82, 88, 89, 100, 101; 600/2, 439, 600/451

(56) References Cited

U.S. PATENT DOCUMENTS

| | | |
|---|---|---|
| 3,275,059 A | 9/1966 | McCullough |
| 3,392,916 A | 7/1968 | Engstrom et al. |
| 3,561,444 A | 2/1971 | Boucher |
| 3,765,606 A | 10/1973 | Moss et al. |
| 3,860,173 A | 1/1975 | Sata |
| 4,052,004 A | 10/1977 | Martin et al. |
| 4,085,893 A * | 4/1978 | Durley, III ............... 239/102.2 |
| 4,153,201 A | 5/1979 | Berger et al. |
| 4,251,031 A | 2/1981 | Martin et al. |
| 4,271,705 A | 6/1981 | Crostack |
| 4,294,407 A | 10/1981 | Reichl et al. |
| 4,301,093 A | 11/1981 | Eck |
| 4,301,968 A | 11/1981 | Berger et al. |
| 4,309,989 A | 1/1982 | Fahim |
| 4,319,155 A | 3/1982 | Nakai et al. |
| 4,334,531 A | 6/1982 | Reichl et al. |
| 4,352,459 A | 10/1982 | Berger et al. |
| 4,428,531 A | 1/1984 | Martin |
| 4,466,571 A | 8/1984 | Muhlbauer |
| 4,530,360 A | 7/1985 | Duarte |
| 4,541,564 A | 9/1985 | Berger et al. |
| 4,582,654 A | 4/1986 | Karnicky et al. |
| 4,619,400 A | 10/1986 | Van Der Burgt |
| 4,642,581 A | 2/1987 | Erickson |
| 4,655,393 A | 4/1987 | Berger |
| 4,659,014 A | 4/1987 | Soth et al. |
| 4,679,551 A | 7/1987 | Anthony |

(Continued)

FOREIGN PATENT DOCUMENTS

EP 0 156 4009 A2 2/1985

(Continued)

OTHER PUBLICATIONS

Journal of Burn Care & Rehabilitation; vol. 21, No. 4; Jul./Aug. 2000 pp. 333-338.

(Continued)

Primary Examiner—Nicholas D. Lucchesi
Assistant Examiner—Michael M Thompson
(74) Attorney, Agent, or Firm—Carter, DeLuca, Farrell & Schmidt, LLP

(57) ABSTRACT

A nozzle for ultrasound wound treatment comprising a main body with proximal and distal ends, a reservoir and valve. The proximal end of the nozzle being removably attached to an ultrasound transducer. The distal end of the nozzle being marginally close and coaxial to the free distal end of the ultrasound transducer. The body of the nozzle connected with liquid reservoir, which holds the wound treatment solution and delivers same to the free end of ultrasound tip directly or through a tube. The nozzle is provided with valve for controlling flow rate of wound treatment solution. The nozzle can mix different liquids or a liquid with a gas and deliver same to the wound surface.

The nozzle can also be provided with trigger system for one hand use. The present invention is a device, using ultrasonic waves to create, direct and deliver liquid treatment spray to a wound surface.

48 Claims, 10 Drawing Sheets

U.S. PATENT DOCUMENTS

| | | |
|---|---|---|
| 4,726,523 A | 2/1988 | Kokubo et al. |
| 4,726,525 A | 2/1988 | Yonekawa et al. |
| 4,733,820 A | 3/1988 | Endo et al. |
| 4,756,478 A | 7/1988 | Endo et al. |
| 4,767,402 A | 8/1988 | Kost et al. |
| 4,783,003 A | 11/1988 | Hirabayashi et al. |
| 4,790,479 A | 12/1988 | Matsumoto et al. |
| 4,793,339 A | 12/1988 | Matsumoto et al. |
| 4,850,534 A | 7/1989 | Takahashi et al. |
| 4,877,989 A | 10/1989 | Drews et al. |
| 4,905,671 A | 3/1990 | Senge et al. |
| 4,930,700 A | 6/1990 | McKown |
| 4,941,618 A | 7/1990 | Hildebrand et al. |
| 4,961,885 A | 10/1990 | Avrahami et al. |
| 5,002,059 A | 3/1991 | Crowley et al. |
| 5,013,241 A * | 5/1991 | von Gutfeld et al. ............ 601/2 |
| 5,040,537 A | 8/1991 | Katakura |
| 5,063,922 A | 11/1991 | Hakkinen |
| 5,076,266 A * | 12/1991 | Babaev .................. 128/200.16 |
| 5,104,042 A | 4/1992 | McKown |
| 5,115,805 A | 5/1992 | Bommannan et al. |
| 5,134,993 A | 8/1992 | van der Linden et al. |
| 5,163,433 A | 11/1992 | Kagawa et al. |
| 5,172,692 A | 12/1992 | Kulow et al. |
| 5,186,162 A | 2/1993 | Talish et al. |
| 5,197,946 A | 3/1993 | Tachibana |
| 5,211,160 A | 5/1993 | Talish et al. |
| 5,231,975 A | 8/1993 | Bommannan et al. |
| 5,269,291 A | 12/1993 | Carter |
| 5,315,998 A | 5/1994 | Tachibana et al. |
| 5,316,000 A | 5/1994 | Chapelon et al. |
| 5,318,014 A | 6/1994 | Carter |
| 5,323,769 A | 6/1994 | Bommannan et al. |
| 5,324,255 A | 6/1994 | Passafaro et al. |
| 5,345,940 A | 9/1994 | Seward et al. |
| 5,347,998 A | 9/1994 | Hodson et al. |
| 5,362,309 A | 11/1994 | Carter |
| 5,374,266 A | 12/1994 | Kataoka et al. |
| 5,380,411 A | 1/1995 | Schlief |
| 5,393,296 A | 2/1995 | Rattner |
| 5,437,606 A | 8/1995 | Tsukamoto |
| 5,515,841 A | 5/1996 | Robertson et al. |
| 5,515,842 A | 5/1996 | Ramseyer et al. |
| 5,516,043 A | 5/1996 | Manna et al. |
| 5,520,166 A | 5/1996 | Ritson et al. |
| 5,520,612 A | 5/1996 | Winder et al. |
| 5,527,350 A | 6/1996 | Grove et al. |
| 5,529,572 A | 6/1996 | Spector |
| 5,545,124 A | 8/1996 | Krause et al. |
| 5,551,416 A | 9/1996 | Stimpson et al. |
| 5,554,172 A | 9/1996 | Horner et al. |
| 5,556,372 A | 9/1996 | Talish et al. |
| 5,573,497 A | 11/1996 | Chapelon |
| 5,616,140 A | 4/1997 | Prescott |
| 5,626,554 A | 5/1997 | Ryaby et al. |
| 5,643,179 A | 7/1997 | Fujimoto |
| 5,656,016 A | 8/1997 | Ogden |
| 5,658,323 A | 8/1997 | Miller |
| 5,699,805 A | 12/1997 | Seward et al. |
| 5,707,402 A | 1/1998 | Heim |
| 5,707,403 A | 1/1998 | Grove et al. |
| 5,730,705 A | 3/1998 | Talish et al. |
| 5,735,811 A | 4/1998 | Brisken |
| 5,743,863 A | 4/1998 | Chapelon |
| 5,752,924 A | 5/1998 | Kaufman et al. |
| 5,762,616 A | 6/1998 | Talish |
| 5,785,972 A | 7/1998 | Tyler |
| 5,835,678 A | 11/1998 | Li et al. |
| 5,843,139 A | 12/1998 | Goedeke et al. |
| 5,879,314 A | 3/1999 | Peterson et al. |
| 5,879,364 A | 3/1999 | Bromfield et al. |
| 5,882,302 A | 3/1999 | Driscoll, Jr. et al. |
| 5,894,841 A | 4/1999 | Voges |
| 5,947,921 A | 9/1999 | Johnson et al. |
| 5,960,792 A | 10/1999 | Lloyd et al. |
| 5,989,245 A | 11/1999 | Prescott |
| 6,001,069 A | 12/1999 | Tachibana et al. |
| 6,014,970 A | 1/2000 | Irvi et al. |
| 6,024,718 A | 2/2000 | Chen et al. |
| 6,026,808 A | 2/2000 | Armer et al. |
| 6,027,495 A | 2/2000 | Miller |
| 6,041,253 A | 3/2000 | Kost et al. |
| 6,061,597 A | 5/2000 | Rieman et al. |
| 6,076,519 A | 6/2000 | Johnson |
| 6,083,159 A | 7/2000 | Driscoll, Jr. et al. |
| 6,095,141 A | 8/2000 | Armer et al. |
| 6,098,620 A | 8/2000 | Lloyd et al. |
| 6,102,298 A | 8/2000 | Bush et al. |
| 6,106,547 A | 8/2000 | Huei-Jung |
| 6,113,558 A | 9/2000 | Rosenschein et al. |
| 6,113,570 A | 9/2000 | Siegel et al. |
| RE36,939 E | 10/2000 | Tachibana et al. |
| 6,158,431 A | 12/2000 | Poole |
| 6,176,839 B1 | 1/2001 | DeLuis et al. |
| 6,186,963 B1 | 2/2001 | Schwarze et al. |
| 6,190,315 B1 | 2/2001 | Kost et al. |
| 6,190,336 B1 | 2/2001 | Duarte et al. |
| 6,206,842 B1 | 3/2001 | Tu et al. |
| 6,206,843 B1 | 3/2001 | Iger et al. |
| 6,231,528 B1 | 5/2001 | Kaufman et al. |
| 6,234,990 B1 | 5/2001 | Rowe et al. |
| 6,251,099 B1 | 6/2001 | Kollias et al. |
| 6,273,864 B1 | 8/2001 | Duarte et al. |
| 6,321,109 B2 | 11/2001 | Ben-Haim et al. |
| 6,322,527 B1 | 11/2001 | Talish |
| 6,325,769 B1 | 12/2001 | Klopotek |
| 6,478,754 B1 * | 11/2002 | Babaev ........................ 604/22 |
| 6,533,803 B2 * | 3/2003 | Babaev ........................ 604/22 |
| 6,569,099 B1 * | 5/2003 | Babaev ...................... 600/439 |
| 6,601,581 B1 * | 8/2003 | Babaev .................. 128/200.16 |
| 6,663,554 B2 * | 12/2003 | Babaev ........................ 600/2 |

FOREIGN PATENT DOCUMENTS

| | | |
|---|---|---|
| EP | 0 437 155 B1 | 2/1990 |
| EP | 0416106 | 3/1991 |
| EP | 0 657 226 B1 | 11/1994 |
| GB | 2 099 710 A | 12/1982 |
| GB | 2 101 500 A | 1/1983 |
| JP | 2000237275 A2 | 9/2000 |
| SU | 1106485 | 10/1982 |
| SU | 1827239 | 5/1990 |
| WO | WO 96/35383 | 11/1996 |
| WO | 97/17933 | 5/1997 |

OTHER PUBLICATIONS

Design and Application of Low-Frequency Ultrasound and Its Combination With Laser Radiation in Surgery and Therapy—Critical Reviews in Biomedical Engineering; 2001; pp. 502-519.

"Comparison Possibilities of Ultrasound and its Combination with Laser in Surgery and Therapy", Zharov et al., Biomedical Optoacoustics, Proceedings of SPIE, vol. 3916 (2000), pp. 331-339.

XP002294548, Abstract corresponding to SU 914099.

European Search Report corresponding to EPO Appln. No. 01973544.8-2107-US0130096.

* cited by examiner

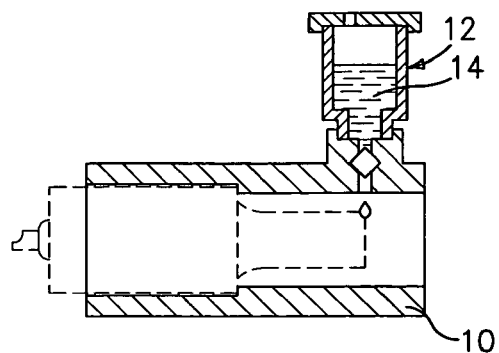
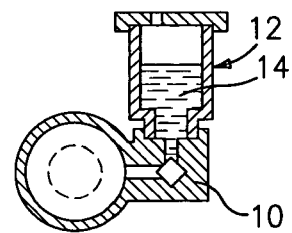
*FIG. 2a*  *FIG. 2b*
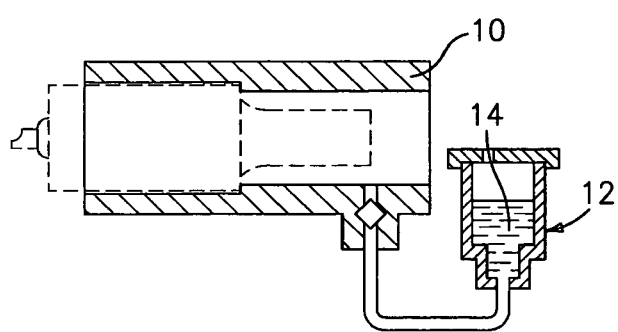
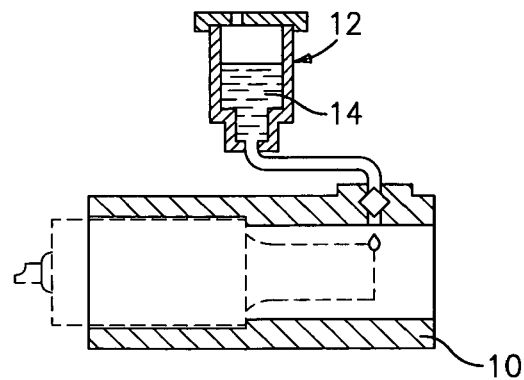
*FIG. 2c*  *FIG. 2d*

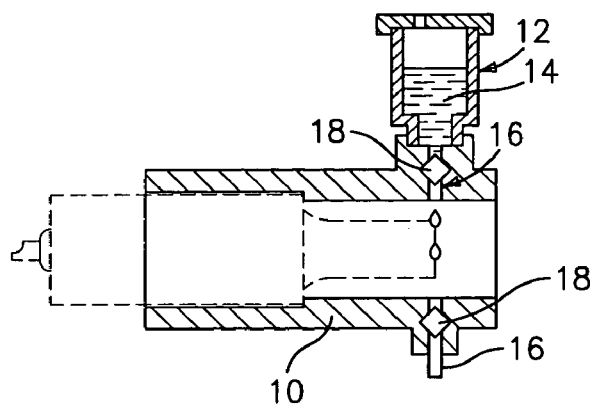
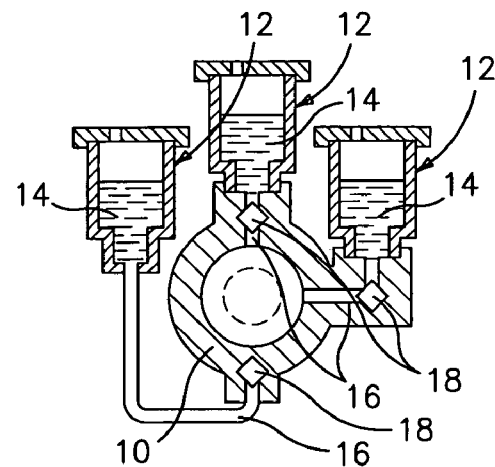
*FIG. 4a*                    *FIG. 4b*
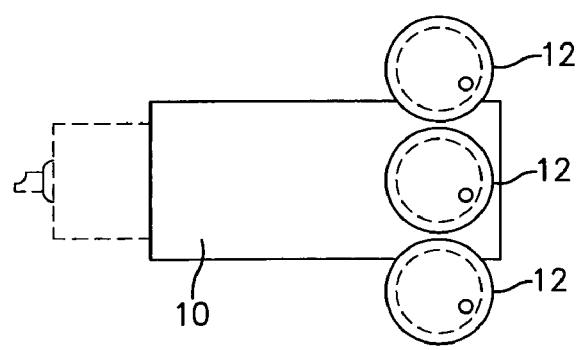
*FIG. 4c*

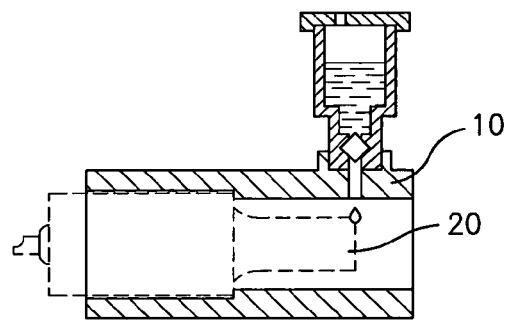
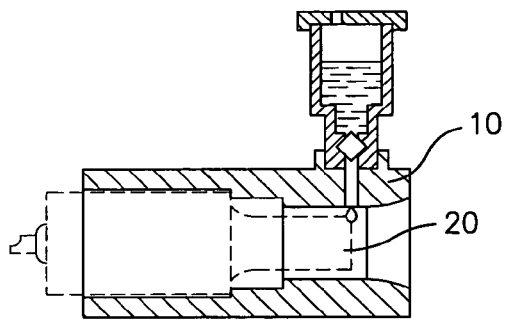
FIG. 8a  FIG. 8b
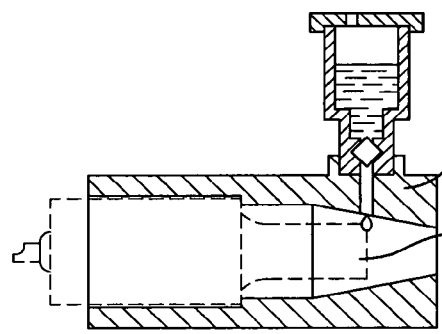 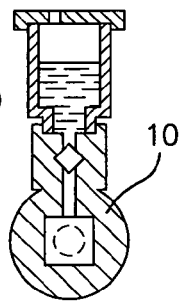 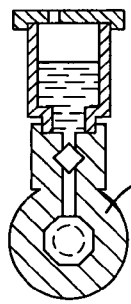 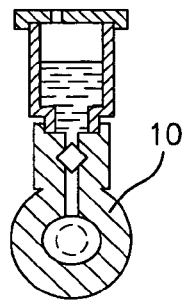
FIG. 8c   FIG. 8d   FIG. 8e   FIG. 8f

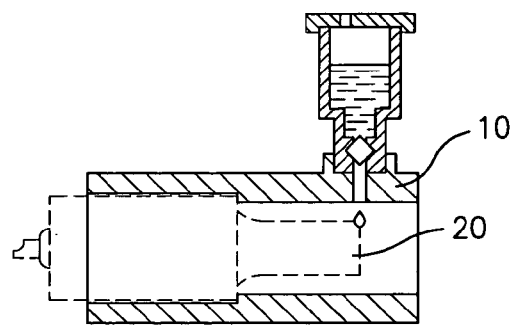
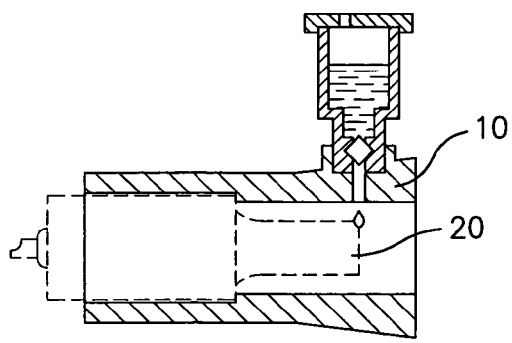
FIG. 9a  FIG. 9b
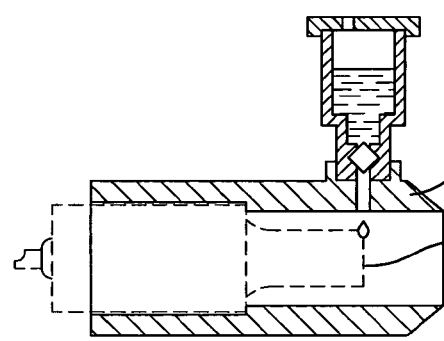
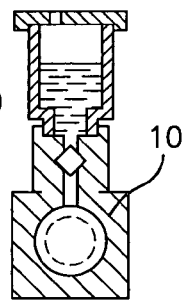
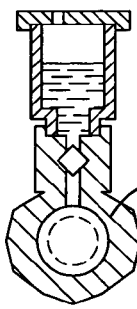
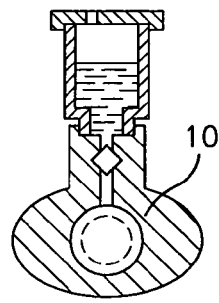
FIG. 9c  FIG. 9d  FIG. 9e  FIG. 9f

NOZZLE FOR ULTRASOUND WOUND TREATMENT

FIELD OF THE INVENTION

The present invention relates to a device for using ultrasonic waves in wound treatment. More particularly, the present invention relates to a device for spraying a wound surface using ultrasonic waves for delivering drugs, killing bacteria, cleansing a surface, and stimulating healthy tissue cells.

BACKGROUND OF THE INVENTION

Ultrasonic waves have been widely used in medical applications, including both diagnostics and therapy as well as in many industrial applications. One diagnostic use of ultrasound waves includes using ultrasonic waves to detect underlying structures in an object or a human tissue. In this procedure, an ultrasonic transducer is placed in contact with the object or tissue via a coupling medium and high frequency (1–10 MHz) ultrasonic waves are directed into the tissue. Upon contact with the various underlying structures, the waves are reflected back to a receiver adjacent to the transducer. By comparison of the signals of the ultrasonic wave as sent with the reflected ultrasonic wave as received, an image of the underlying structure can be produced. This technique is particularly useful for identifying boundaries between components of tissue and can be used to detect irregular masses, tumors and the like.

Two therapeutic medical uses of ultrasound waves include aerosol mist production and contact physiotherapy. Aerosol mist production makes use of a nebulizer or inhaler to produce an aerosol mist for creating a humid environment and delivering drugs to the lungs. Ultrasonic nebulizers operate by the passage of ultrasound waves of sufficient intensity through a liquid, the waves being directed at an air-liquid interface of the liquid from a point underneath or within the liquid. Liquid particles are ejected from the surface of the liquid into the surrounding air following the disintegration of capillary waves produced by the ultrasound. This technique can produce a very fine dense fog or mist. Aerosol mists produced by ultrasound are preferred over aerosol mists produced by other methods because a smaller particle size of the aerosol can be obtained with the ultrasonic waves. One of the major shortcomings of inhalers and nebulizers is that the aerosol mist cannot be directed to a target area without an air stream which decreases the efficiency of ultrasound.

Ultrasonic sprayers such as those sold by Sonic and Materials Inc., Misonix Inc., Sono-Tek Inc., and Zervex International, Inc. (see, for example, U.S. Pat. Nos. 3,765,606, 4,659,014, 5,104,042, 4,930,700, 4,153,201, 4,655,393, 5,516,043, 5,835,678, Ultrasonic inhalers and drug delivery systems from Medisonic USA, Inc., 3M, Siemens Gmb, The Procter & Gamble Company, Sheffield Pharmaceuticals, and Aradigm, Inc. (see, for example, U.S. Pat. Nos. 4,294,407, 5,347,998, 5,520,166, 5,960,792, 6,095,141, 6,102,298, 6,098,620, 6,026,808, and 6,106,547) operate by atomizing liquid using piezoceramic film. Although some inhalers and delivery systems use nozzles, the nozzles are just for directing the atomized liquid to the mouth by touching the lips. These nozzles do not create any spray, and the inhaler and drug delivery systems can work without them.

OBJECTS OF THE INVENTION

It is an object of this invention to provide an improved device for treating wounds.

It is also an object of this invention to provide an improved device for treating wounds using ultrasonic waves.

It is a further object of the invention to provide a device for creating, directing and delivering liquid aerosol spray to a wound surface.

It is yet a further object of the invention to provide a device for creating ultrasonic waves and delivering drugs, killing bacteria, cleansing a surface, and/or stimulating healthy tissue.

These and other objects of the invention will become more apparent from the more detailed discussion below.

SUMMARY OF THE INVENTION

The present invention relates to a device using ultrasonic waves to create, direct and deliver liquid aerosol spray to a wound surface. More particularly, the present invention relates to an emission device comprising a nozzle which is a preferably cylindrical, but optionally can be multiangular, from the inside and is cylindrical, rectangular or multiangular from the outside distal end; a liquid reservoir; and a different shaped proximal end to be removably attached to ultrasound transducer.

The liquid reservoir is provided with a valve, which works as a dispenser and allows liquid to reach the ultrasound tip as drops or via continuous flow through an orifice and a gap.

The proximal end of the nozzle can be connected to the transducer housing in a variety of different ways, such as by threads, bolts or screwed on, snap/friction fit, or by other means.

The liquid reservoir portion of the nozzle can be attached to the top, side, or bottom of the nozzle body or located outside the nozzle body. Liquid from the reservoir may be delivered under gravity, or by motorized pump. The liquid reservoir can be elastic or rigid, with or without a cover, and can be made from a variety of different materials, such as, for example, metal, plastic, rubber, ceramic, or other suitable material, and is provided with metered dose device or a liquid dispenser.

The liquid reservoir can provide the free end of an ultrasound transducer tip with liquid/solution directly from inside the distal end of the nozzle, or through an orifice or a tube from the front end of the nozzle.

The nozzle can be provided with two, three or more reservoirs or tubes, for mixing different liquids, drugs or liquid(s) with gas. For example, saline can be mixed with oxygen and used to treat a wound. Gas and liquid can be delivered separately from the top, side and bottom of the distal end of the ultrasound transducer to be mixed and sprayed on the wound surface.

The valve part of the nozzle can be located between the reservoir and nozzle body, inside of the reservoir, or inside of the nozzle. The nozzle can optionally be provided with a trigger connecting and operating the valve. This design allows a user to operate the device with one hand. The trigger can be located on the top, side or bottom of the nozzle.

The nozzle can work without a valve, if, for example, the reservoir is made from an elastic rubber material. In this case liquid from the reservoir is delivered by squeezing the elastic reservoir.

The main body and distal end of the nozzle may be cylindrical, oval, elliptic, conical, rectangular or multiangular from the inside.

From the outside, the main body and distal end of the nozzle can be any shape such as, for example, a cylinder, cut cylinder, cone, cut cone, concave, double cut, rectangular, multiangular or a combination of these shapes.

The proximal end of the nozzle can be any shape, but must be removably attachable to the ultrasound transducer, for example, via threads, friction fit, screws, slots, spline, or other means.

The shape of the distal end of the nozzle as viewed from the horizontal side can be cylindrical, a cut cylinder, conical, a double cut cylinder or cone, spherical, elliptic/oval or curved, multiangular, waved or a combination of these shapes.

Finally the ultrasound wound treatment nozzle can be comprised of many different parts, such as a body/housing, reservoir, valve, and dispenser, or formed in one solid part.

While the invention has been described in general terms, the construction and obvious advantages of the device will be more clearly understood with reference to the following description of the various specific embodiments when read in conjunction with the accompanying drawings.

BRIEF DESCRIPTION OF THE DRAWINGS

FIG. 2a) is a cross-sectional view of the nozzle of FIG. 1 with the liquid reservoir located in the preferred top position.

FIG. 2b) is a cross-sectional end view of the nozzle of FIG. 1 with the liquid reservoir located in the side position.

FIG. 2c) is another cross-sectional view of the nozzle of FIG. 1 with the liquid reservoir located in the bottom position.

FIG. 2d) is another cross-sectional view of the nozzle of FIG. 1 with the liquid reservoir located to one side of the preferred top position.

FIG. 4a) is a cross-sectional view of the nozzle of FIG. 1 showing the nozzle with multiple liquid entry points.

FIG. 4b) is top plan view of the nozzle according to the invention showing three liquid/fluid reservoirs located side by side.

FIG. 4c) is a cross-sectional end elevation view of the nozzle depicted in FIGS. 4a and 4b showing the three reservoirs located side by side with three separate entry points located at different points around the nozzle.

FIG. 8a) is a cross-sectional elevation of the nozzle of FIG. 1 showing the distal end of the nozzle with a cylindrical shape.

FIG. 8b) is a cross-sectional elevation of the nozzle of FIG. 1 showing the distal end of the nozzle with an oval shape.

FIG. 8c) is a cross-sectional elevation of the nozzle of FIG. 1 showing the distal end of the nozzle with a conical shape.

FIG. 8d) is a cross-sectional end view of the nozzle of FIG. 1 showing the distal end with a rectangular section.

FIG. 8e) is a cross-sectional end view of the nozzle of FIG. 1 showing the distal end of the nozzle with a multi-angular section.

FIG. 8f) is a cross-sectional end view of the nozzle of FIG. 1 showing the distal end of the nozzle with an oval section.

FIG. 9a) is a cross-sectional elevation view of the nozzle of FIG. 1 showing the outside shape of the nozzle as a cylinder.

FIG. 9b) is a cross-sectional elevation view of the nozzle of the invention showing the outside of the nozzle as a flared cylinder.

FIG. 9c) is a cross-sectional elevation view of the nozzle of the invention showing the outside of the nozzle having a conical distal end.

FIG. 9d) is a cross-sectional elevation view of the nozzle of the invention showing the outside of the nozzle with a concave distal end.

FIG. 9e) is a cross-sectional elevation view of the nozzle of the invention showing the outside of the nozzle with a double cut profile.

FIG. 9f) is a cross-sectional elevation view of the nozzle of the invention showing the outside of the nozzle with an oval profile.

DETAILED DESCRIPTION OF THE PREFERRED EMBODIMENTS

The present invention is a device which uses ultrasonic waves to create, direct and deliver liquid spray to a wound surface comprising a nozzle. The nozzle for ultrasound wound treatment includes a nozzle body having a proximal end which can be removably attached to an ultrasound transducer, the distal end of said nozzle body to be adjacent to the ultrasound transducer tip. The nozzle comprises a generally cylindrical main body and a reservoir in which wound treatment liquid/solution is filled and a valve for dispensing and delivering the liquid/solution to the distal end of ultrasound tip.

Figure 1:
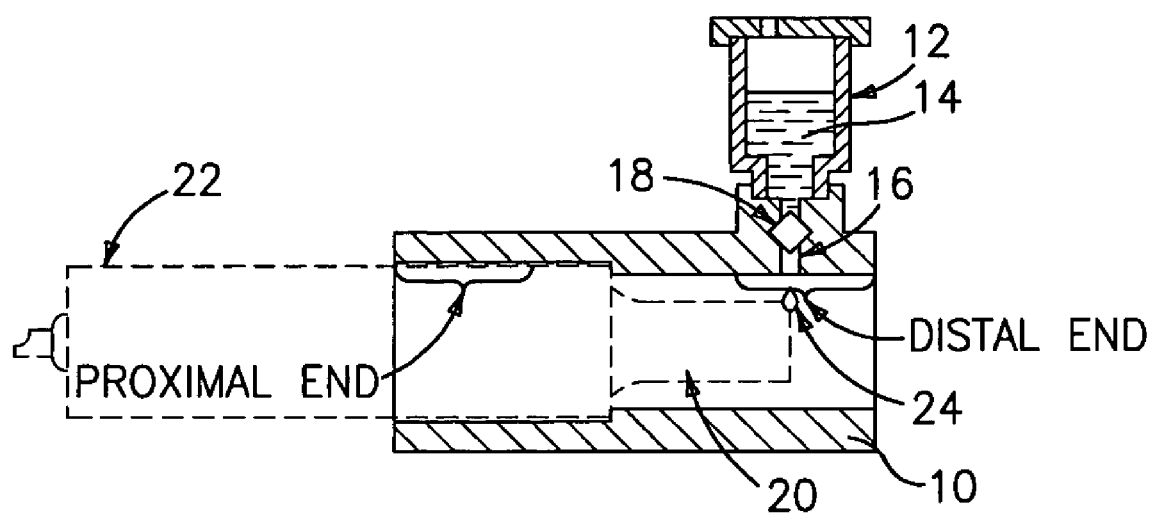
FIG. 1 is a cross-sectional view of a side elevation of a preferred embodiment of the nozzle and fluid reservoir for ultrasound wound treatment according to the invention.

The invention can perhaps be better appreciated from the drawings. A nozzle for ultrasound wound treatment according to the present invention is illustrated in FIG. 1. More particularly, FIG. 1 depicts a cross-sectional view of a side elevation of a preferred embodiment of the nozzle for ultrasound wound treatment, with a main body 10 of the nozzle, a wound treatment liquid/solution reservoir 12, and a retaining wound treatment liquid/solution 14 which is inter-connected via a tube 16, controlled by a valve 18 to deliver a supply of treatment liquid/solution droplets 24 to the distal end of an ultrasound tip 20 of an ultrasound transducer 22. Wound treatment liquid 14 from reservoir 12 is dispensed and delivered by valve 18 to contact distal end of ultrasound tip 20 and spray onto the wound surface.

FIGS. 2a)–d) illustrate possible locations of liquid reservoir 12 relative to nozzle body 10. The preferred location of reservoir 12 is on the top of nozzle body 10, as illustrated in FIG. 2a), since this arrangement is most convenient, easy to handle and space-saving. Reservoir 12 may optionally be provided with a cover.

Figure 3A:
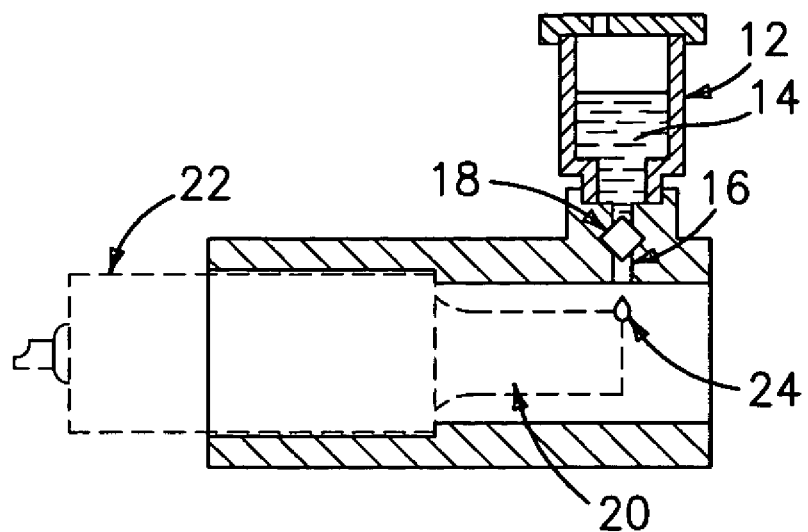
FIG. 3a) is a cross-sectional elevation view of the nozzle of FIG. 1 with the reservoir providing the tip of the nozzle with liquid directly from inside.
Figure 3B:
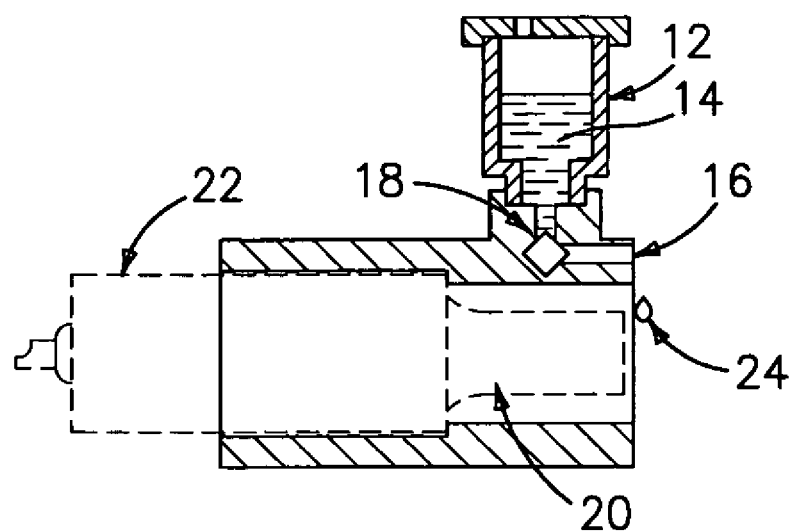
FIG. 3b) is another cross-sectional elevation view of the nozzle of FIG. 1 with the reservoir providing the tip of the nozzle with liquid through an orifice or tube from the front end of the nozzle.

FIGS. 3a) and b) depict alternative cross-sectional views of nozzle body 10 and reservoir 12, providing ultrasound tip 20 with liquid/solution directly and through orifice tube 16.

FIGS. 4a)–c), collectively depict side and end elevation views and top views of a three reservoir system for mixing different liquids, drugs, or liquids and gases, for example, saline with oxygen, and treating a wound. Shown are nozzle body 10 and multiple liquid/fluid reservoirs 12, with liquid/fluid treatments 14 being fed via tubes 16 and controlled by valves 18.

Gas and liquid can be delivered separately from the top, side and bottom of the distal end of the ultrasound transducer to be mixed and sprayed on the wound surface. This design allows one to mix different liquids and/or liquids with gas, such as saline or an antibiotic with oxygen during wound treatment, without the use of high pressure, which is required with other mixing methods.

Figure 5A:
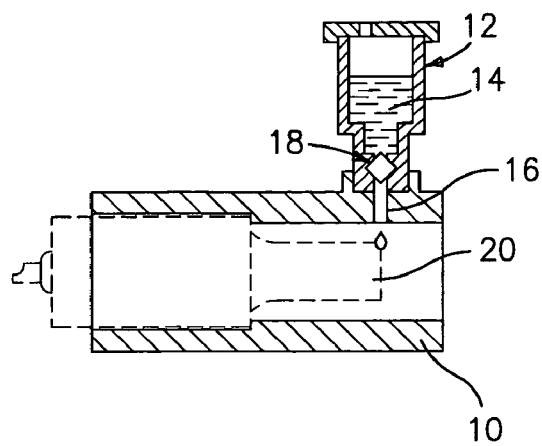
FIG. 5a) is a cross-sectional elevation view of the nozzle of FIG. 1 showing the control valve located within the housing of the liquid reservoirs.

FIGS. 5a)–c), collectively depict various locations for the placement of valve 18 between reservoir 12 and tube 16 which delivers liquid/fluid to the distal end of ultrasound transducer tip 20.

Figure 5B:
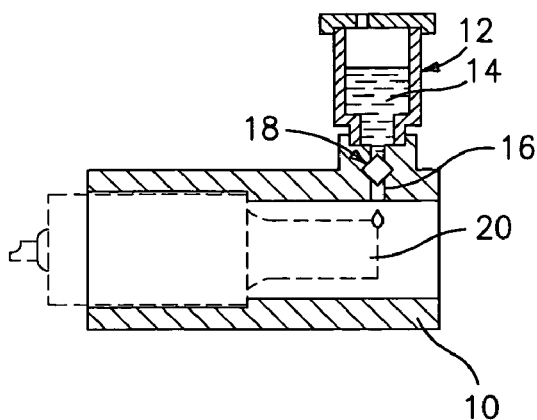
FIG. 5b) is a cross-sectional elevation view of the nozzle of FIG. 1 showing the control valve located outside the body of the liquid reservoir, but within the body housing of the nozzle.
Figure 5C:
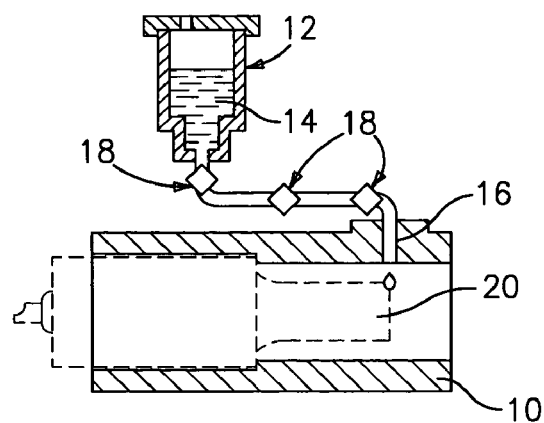
FIG. 5c) is a cross-sectional elevation view of the nozzle of FIG. 1 showing the control valve located at various points along the transfer tube.

To avoid liquid loss during dispensing, the distance from valve 18 to the distal end of ultrasound transducer tip 20 should be minimized. This means that valve 18 should be located as close as possible to the distal end of the ultrasound transducer tip 20. For this reason, the most preferred location is as shown in FIG. 5b).

Figure 6:
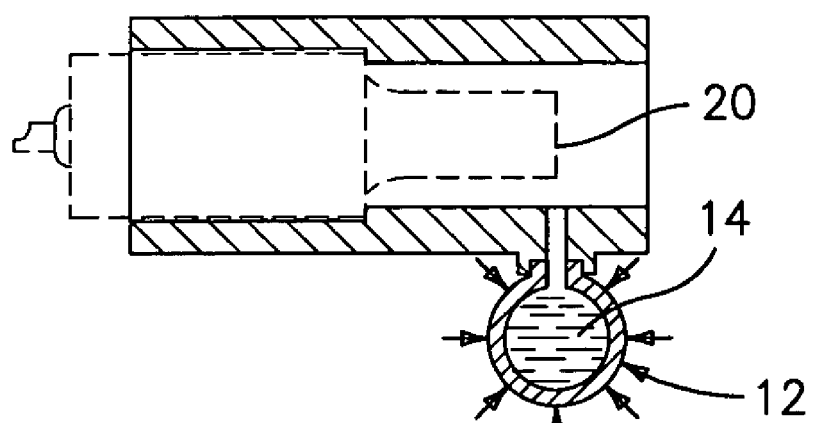
FIG. 6 is a cross-sectional elevation view of the nozzle of FIG. 1 showing the liquid reservoir in the bottom position without a control valve, where the fluid is delivered via squeezing on a flexible liquid reservoir.

FIG. 6 depicts a cross-sectional elevation view of another preferred embodiment of the nozzle of the invention without valve 18. In this configuration reservoir 12 must be constructed of an elastic material and liquid 14 will be delivered to the ultrasound transducer tip 20 by squeezing the walls of reservoir 12. Reservoir 12 can be rigid, but liquid must the reach the ultrasound tip 20 using a different means.

Figure 7:
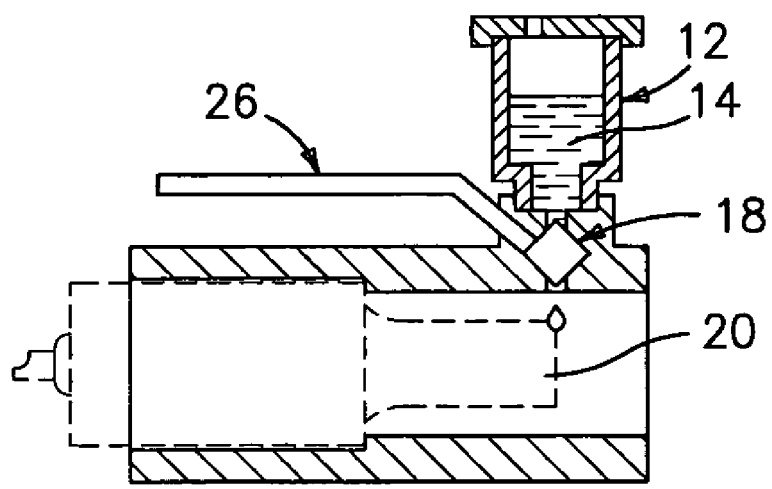
FIG. 7 is a cross-sectional side elevation view of the nozzle of FIG. 1 with the fluid reservoir in the top position employing a trigger to open/close the control valve.

FIG. 7 depicts a cross-sectional elevation view of nozzle body 10 with a trigger 26, which is connected and operates valve 18, thus dispensing and changing liquid flow.

FIGS. 8a)–f), collectively depict various alternative preferred nozzle 10 geometries.

The shape of the distal end of nozzle 10 from inside can be cylindrical, as shown in FIG. 8a), conical, as shown in FIGS. 8b) and c), (back or forward), rectangular, as shown in FIG. 8d), multiangular, as shown in FIG. 8e), elliptic-oval as shown in FIG. 8f), or a combination of different shapes. The most preferred shape is cylindrical because of the uniform gap created between distal end of nozzle 10 and cylindrical ultrasound tip 20, with this shape.

FIGS. 9a)–f), collectively depict various alternative preferred nozzle 10 geometries from the outside. The shape of the distal end of nozzle 10 from outside can be cylindrical, as shown in FIG. 9a), conical as depicted in FIGS. 9b)–c), rectangular as shown in FIG. 9), multiangular as shown in FIG. 9e), elliptic/oval as shown in FIG. 9f) or a combination of different shapes.

Figure 10A:
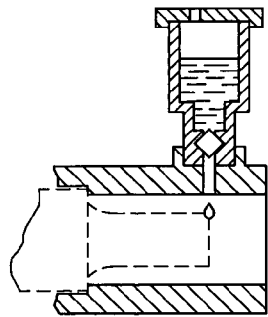
FIG. 10a) is a cross-sectional elevation view of the nozzle of FIG. 1 showing the distal end of the nozzle with a rectangular cut shape.
Figure 10B:
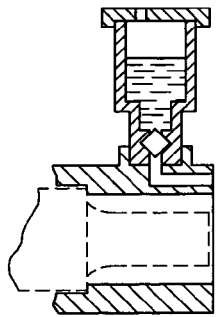
FIG. 10b) is a cross-sectional elevation view of the nozzle of FIG. 1 showing the distal end of the nozzle with a cylindrical cut shape.
Figure 10C:
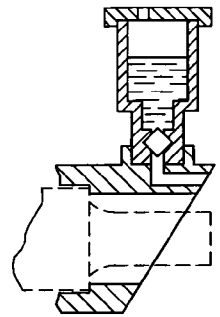
FIG. 10c) is a cross-sectional elevation view of the nozzle of FIG. 1 showing the distal end of the nozzle with a conical cut shape.
Figure 10D:
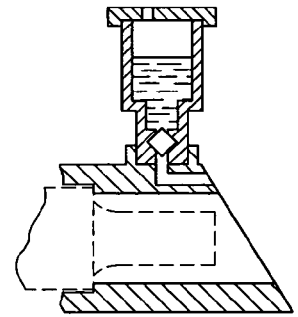
FIG. 10d) is a cross-sectional elevation view of the nozzle of FIG. 1 showing the distal end of the nozzle with a spherical elliptical oval cut shape.
Figure 10E:
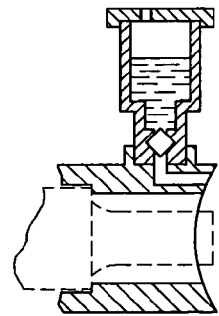
FIG. 10e) is a cross-sectional elevation view of the nozzle of FIG. 1 showing the distal end of the nozzle with a concave cut shape.
Figure 10F:
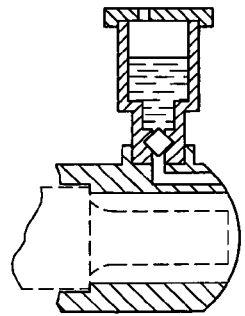
FIG. 10f) is a cross-sectional elevation view of the nozzle of FIG. 1 showing the distal end of the nozzle with a convex shape.
Figure 10G:
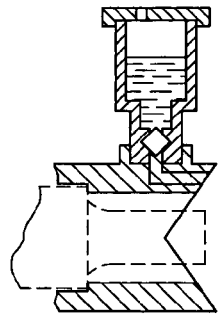
FIG. 10g) is a cross-sectional elevation view of the nozzle of FIG. 1 showing the distal end of the nozzle with a double cut shape.
Figure 10H:
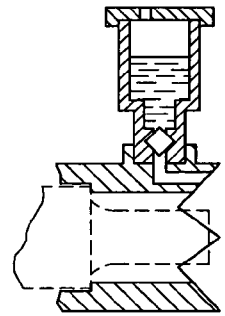
FIG. 10h) is a cross-sectional elevation view of the nozzle of FIG. 1 showing the distal end of the nozzle with a waved cut shape.

FIGS. 10a)–h) depict cross-sectional elevational views of the distal end of nozzle showing the different shapes possible, a rectangle as shown in FIG. 10a), cut cylinder as shown in FIGS. 10b)–c), spherical/elliptic/oval as shown in FIG. 10d), concave as shown in FIG. 10e), convex as shown in FIG. 10f), double cut as shown in FIG. 10g), waved as shown in FIG. 10h) or a combination of different shapes.

Figure 11:
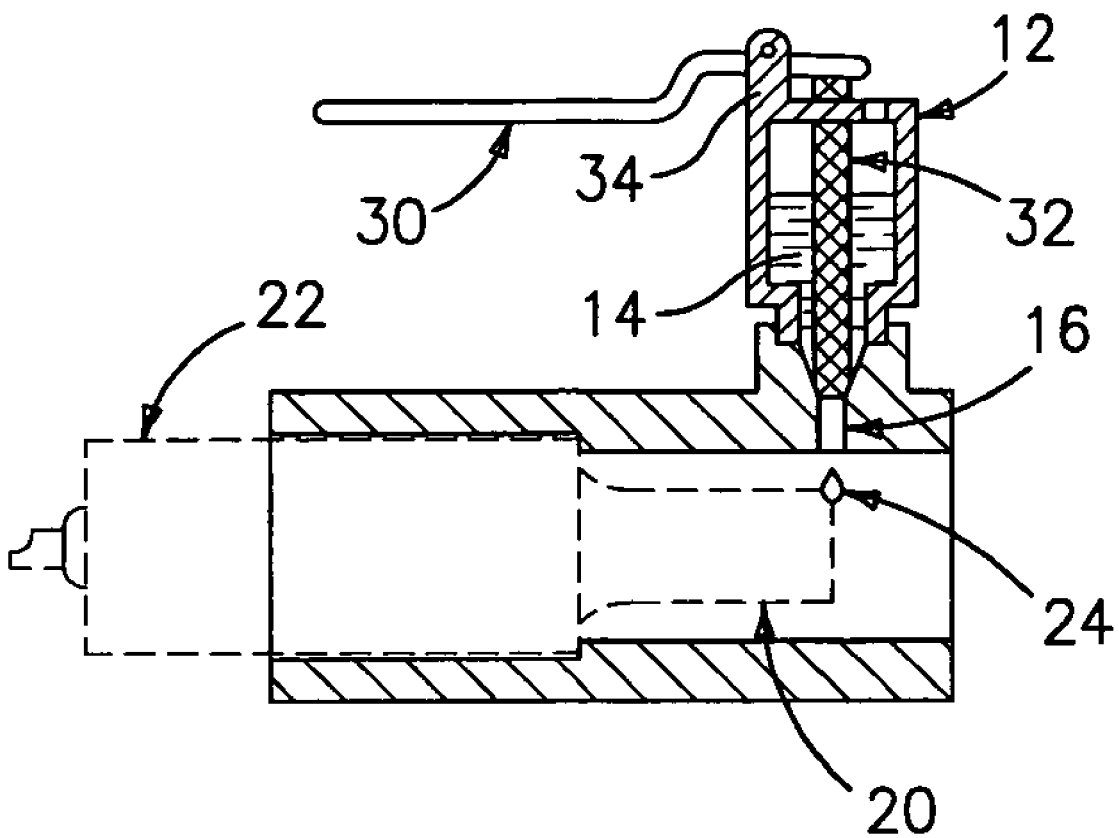
FIG. 11 is a cross-sectional elevation view of one preferred embodiment of a self destructing disposable nozzle according to the invention.

With reference to FIG. 11, shown is one preferred embodiment of a self-destructing disposable nozzle fabricated from one-piece plastic. A trigger 30 with a needle valve 32 connected with reservoir 12 at a point 34 in closing position. After reservoir 12 is filled with liquid and positioning at the wound, trigger 30 is depressed opening valve 32 by lifting. Because of the rigid connection of trigger 30 to reservoir 12, after pushing trigger 30 gets broken at point 34, and after the first procedure is done, will no longer retain the liquid in reservoir 12. Thus, this becomes a one use disposable reservoir/nozzle arrangement.

The preceding specific embodiments are illustrative of the practice of the invention. It is to be understood, however, that other expedients known to those skilled in the art or disclosed herein, may be employed without departing from the spirit of the invention or the scope of the appended claims.

What is claimed is:

1. A removable nozzle for ultrasound wound treatment, for producing a spray of liquid using an ultrasound transducer having a tip, directing and delivering said spray onto the wound surface, comprising:
   a main body supported on an ultrasound transducer, the main body having a proximal end that removably attaches to a housing of the ultrasound transducer,
   said main body also having a distal end which is marginally close to a distal end of the ultrasound transducer tip,
   said distal end of said main body having a gap with said distal end of said ultrasound transducer tip,
   said distal end of said main body being coaxially placed about said ultrasound transducer tip,
   said main body defining an opening and being connected with at least one reservoir, for holding and delivering a wound treatment solution at a most distal end of said ultrasound transducer tip via said opening disposed about the most distal end of the ultrasound transducer tip for producing said spray, wherein said spray is delivered through said nozzle.

2. A nozzle according to claim 1, wherein said main body is connected with two or more reservoirs, holding and delivering different wound treatment solutions separately to the distal end or marginally close radial side of said ultrasound transducer tip to be mixed and sprayed onto the wound.

3. A nozzle according to claim 1, wherein said main body is connected with at least one reservoir and at least one gas tube, for delivering different wound treatment solutions and gas separately to the distal end or marginally close radial side of said ultrasound transducer tip to be mixed and sprayed onto the wound.

4. A nozzle for ultrasound wound treatment according to claim 1 for producing a spray of liquid using an ultrasonic transducer tip, directing and delivering said spray onto said wound surface, further comprising a valve for controlling flow rate.

5. A nozzle according to claim 4, wherein said main body has a trigger for controlling the position of said valve.

6. A nozzle according to claim 1, wherein a distal end of the nozzle from the inside is cylindrical.

7. A nozzle according to claim 1, wherein a distal end of nozzle from inside is cone.

8. A nozzle according to claim 1, wherein the distal end of the nozzle from the inside is oval.

9. A nozzle according to claim 1, wherein the distal end of the nozzle from the inside is elliptic.

10. A nozzle according to claim 1, wherein the distal end of the nozzle from the inside is rectangular.

11. A nozzle according to claim 1, wherein the distal end of the nozzle from the inside is multiangular.

12. A nozzle according to claim 1, wherein the distal end of the nozzle from the inside is threaded.

13. A nozzle according to claim 1, wherein the distal end of the nozzle from the inside is combination of different form.

14. A nozzle according to claim 1, wherein the distal end of the nozzle from the outside is cylindrical.

15. A nozzle according to claim 1, wherein the distal end of the nozzle from the outside is cone.

16. A nozzle according to claim 1, wherein the distal end of the nozzle from the outside is oval.

17. A nozzle according to claim 1, wherein the distal end of the nozzle from the outside is elliptic.

18. A nozzle according to claim 1, wherein the distal end of the nozzle from the outside is rectangular.

19. A nozzle according to claim 1, wherein the distal end of the nozzle from the outside is multiangular.

20. A nozzle according to claim 1, wherein the distal end of the nozzle from outside is a combination of different forms.

21. A nozzle according to claim 1, wherein the main body of the nozzle has a reservoir on the top.

22. A nozzle according to claim 1, wherein the main body of the nozzle has a reservoir on the bottom.

23. A nozzle according to claim 1, wherein the main body of the nozzle has a reservoir on the side.

24. A nozzle according to claim 1, wherein the main body of the nozzle is connected with the said reservoir via hose/tube.

25. A nozzle according to claim 1, wherein the main body of the nozzle has a rigidly connected reservoir.

26. A nozzle according to claim 1, wherein the main body of the nozzle has an elastic reservoir.

27. A nozzle according to claim 2, wherein a valve is located in main body of the said nozzle.

28. A nozzle according to claim 2, wherein a valve is located in the said reservoir.

29. A nozzle according to claim 2, wherein a valve is located between the said reservoir and said main body of the nozzle.

30. A nozzle according to claim 1, wherein said nozzle has no valve and liquid is delivered from said reservoir to the distal end of ultrasound transducer tip via a pump or mechanical squeezing.

31. A nozzle according to claim 1, wherein said nozzle is made from distinct pieces.

32. A nozzle according to claim 1, wherein said nozzle is made from one piece.

33. A nozzle according to claim 1, wherein the shape of the distal end of the said main body is a rectangle.

34. A nozzle according to claim 1, wherein the shape of the distal end of the said main body is a cut.

35. A nozzle according to claim 1, wherein the shape of the distal end of the said main body is a double cut.

36. A nozzle according to claim 1, wherein the shape of the distal end of the said main body is a spherical/elliptic/oval.

37. A nozzle according to claim 1, wherein the shape of the distal end of the said main body is waved.

38. A nozzle according to claim 1, wherein the shape of the distal end of the said main body is a combination of different form.

39. A nozzle according to claim 1, wherein the nozzle is self destructing with the first use.

40. A nozzle according to claim 1, wherein the nozzle is sterile.

41. A nozzle according to claim 1, wherein the nozzle is sterilizable.

42. A nozzle according to claim 1, wherein the nozzle is disposable.

43. A nozzle according to claim 1, wherein a part of nozzle is disposable.

44. An apparatus for treating a wound comprising:
   a transducer having a most distal end, said most distal end having a distal radiation surface configured for being arranged in proximity to the surface of the wound and for emitting ultrasonic energy; and
   a removable nozzle comprising:
      a fluid source; and
      a main body supported on said transducer, said main body having a proximal end that removably attaches to a housing of said transducer and a distal end coaxially placed about said most distal end of said transducer, said distal end of said main body defining an opening in fluid communication with said fluid source and disposed about said most distal end of said transducer to produce a spray;
   wherein the generated ultrasonic energy is delivered to the wound through the spray which passes through said nozzle, and wherein the ultrasonic energy provides a bactericidal and a therapeutic effect for decreasing the healing time for the wound.

45. The apparatus according to claim 44, wherein the fluid includes one or more components selected from the group consisting of gas, drugs, liquid, and saline.

46. The apparatus according to claim 44, wherein the therapeutic effect is selected from the group consisting of delivering at least one medicament to the wound, cleansing a surface of the wound, and stimulating healthy tissue cells.

47. The apparatus according to claim 44, wherein the distal radiation surface is threaded.

48. A removable nozzle for ultrasound wound treatment comprising:
   a holder configured and dimensioned for receiving and holding a liquid reservoir;
   a liquid propagation path defining a dispensing orifice and in fluid communication with the liquid reservoir for directing liquid from within the liquid reservoir to a most distal end of an ultrasound transducer via the dispensing orifice, wherein said ultrasound transducer is positioned within the nozzle for producing an ultrasonic spray and wherein said dispensing orifice is disposed about the most distal end of said ultrasound transducer; and
   a housing dimensioned for removably attaching to said ultrasound transducer, for housing at least a portion of the ultrasound transducer, for defining at least a portion of said liquid propagation path defining said dispensing orifice, and for directing the ultrasonic spray through said nozzle towards a wound surface, wherein said housing is supported by said ultrasound transducer.

* * * * *